(12) United States Patent
Besson

(10) Patent No.: US 10,178,980 B2
(45) Date of Patent: Jan. 15, 2019

(54) RADIATION SOURCES AND DETECTOR ARRAY FOR IMAGING MODALITY

(71) Applicant: Analogic Corporation, Peabody, MA (US)

(72) Inventor: Guy M. Besson, Peabody, MA (US)

(73) Assignee: Analogic Corporation, Peabody, MA (US)

( * ) Notice: Subject to any disclaimer, the term of this patent is extended or adjusted under 35 U.S.C. 154(b) by 788 days.

(21) Appl. No.: 14/309,211

(22) Filed: Jun. 19, 2014

(65) Prior Publication Data

US 2015/0366522 A1  Dec. 24, 2015

(51) Int. Cl.
*A61B 6/03* (2006.01)
*A61B 6/00* (2006.01)

(52) U.S. Cl.
CPC ........... *A61B 6/4452* (2013.01); *A61B 6/032* (2013.01); *A61B 6/4007* (2013.01); *A61B 6/4014* (2013.01)

(58) Field of Classification Search
CPC ..... A61B 6/032; A61B 6/4014; A61B 6/4452; A61B 6/4007; A61B 6/027; A61B 6/482; A61B 6/035; A61B 6/4429; G01N 23/046; G01V 5/005
See application file for complete search history.

(56) References Cited

U.S. PATENT DOCUMENTS

| | | | |
|---|---|---|---|
| 4,150,293 A | 4/1979 | Franke | |
| 4,158,142 A | 6/1979 | Haimson | |
| 4,196,352 A * | 4/1980 | Berninger | A61B 6/032 378/10 |
| 4,361,901 A * | 11/1982 | Daniels | A61B 6/02 378/106 |
| 4,993,055 A | 2/1991 | Rand et al. | |
| 5,703,921 A * | 12/1997 | Fujita | A61B 6/4488 378/15 |
| 7,020,233 B1 | 3/2006 | Tybinkowski et al. | |
| 2002/0015470 A1* | 2/2002 | Tybinkowski | A61B 6/4447 378/17 |
| 2002/0037068 A1* | 3/2002 | Oikawa | A61B 6/032 378/15 |
| 2003/0048868 A1* | 3/2003 | Bailey | A61B 6/022 378/65 |
| 2003/0076927 A1* | 4/2003 | Nakashima | A61B 6/032 378/65 |

(Continued)

OTHER PUBLICATIONS

Robb, et al., "High-speed three-dimensional x-ray computed tomography: the dynamic spatial reconstructor," Proc. IEEE, vol. 71, No. 3, pp. 308-319 , Mar. 1983, http://ieeexplore.ieee.org/cart/download.jsp?partnum=1456857&searchProductType=IEEE%20Journals%20Magazines.

(Continued)

*Primary Examiner* — Glen Kao
(74) *Attorney, Agent, or Firm* — TraskBritt

(57) ABSTRACT

A radiation system includes a first rotating unit that rotates about a first axis of rotation. The first rotating unit includes a first radiation source that generates radiation within a first radiation spectrum. The radiation system includes a second rotating unit that rotates about a second axis of rotation. The second rotating unit includes a detector array that detects at least a portion of the radiation generated by the first radiation source. The first and second rotating units may rotate, synchronously, asynchronously, at the same speed and/or at different speeds relative to one another.

20 Claims, 12 Drawing Sheets

(56) References Cited

U.S. PATENT DOCUMENTS

| | | | |
|---|---|---|---|
| 2005/0226364 A1* | 10/2005 | Bernard De Man | A61B 6/032 378/9 |
| 2007/0071163 A1* | 3/2007 | Sakuta | A61B 6/032 378/19 |
| 2010/0002829 A1* | 1/2010 | Dafni | A61B 6/032 378/9 |
| 2010/0310040 A1* | 12/2010 | Hsieh | A61B 6/032 378/17 |
| 2010/0322373 A1* | 12/2010 | Churilla | H04N 1/00127 378/4 |
| 2011/0075814 A1* | 3/2011 | Boese | A61B 6/4007 378/122 |
| 2011/0261926 A1* | 10/2011 | Hangartner | A61B 6/032 378/19 |
| 2013/0077737 A1* | 3/2013 | Fasoli | G01N 23/04 378/4 |
| 2013/0251097 A1* | 9/2013 | Zou | A61B 6/032 378/9 |
| 2014/0140478 A1* | 5/2014 | Hsieh | A61B 6/06 378/62 |
| 2015/0146844 A1* | 5/2015 | Zamyatin | A61B 6/032 378/5 |

OTHER PUBLICATIONS

Goyd, et al., "Cardiac computed tomography," Proc. IEEE, vol. 71, No. 3, pp. 298-307, Mar. 1983, http://ieeexplore.ieee.org/cart/download.jsp?partnum=1456856&searchProductType=IEEE%20Journals%20Magazines.

Saint-Felix et al., "In vivo evaluation of a new system for 3D computerized angiography," Phys. Med. Biol. vol. 39, pp. 583-595, 1994.

Flohr et al., "First performance evaluation of a dual-source CT (DSCT) system," Eur. Radiol., vol. 16, pp. 256-268, 2006.

Papoulis, Athanasios, Probability, random variables and stochastic processes. 3thd Ed., McGraw-Hill, 1991, pp. 1-71.

Schardt et al., "New x-ray tube performance in computed tomography by introducing the rotating envelope tube technology," Med. Phys., vol. 31, No. 9, pp. 2699-2706, Sep. 2004.

Kalender, W.A., "Computed Tomography". 3thd Ed., Publicis, 2011, pp. 1, photo.

Robb, et al., "The Dynamic Spatial Reconstructor A Computed Tomography System for High-Speed Simultaneous Scanning of Multiple Cross Sections of the Heart", Journal of Medical Systems. vol. 4, No. 2. 1980, pp. 253-288.

* cited by examiner

RADIATION SOURCES AND DETECTOR ARRAY FOR IMAGING MODALITY

BACKGROUND

The present application relates to one or more rotatable gantries for radiation imaging modalities that utilize radiation to examine an object. It finds particular application in the field of computed tomography (CT) imaging utilized in medical, security, and/or industrial applications, for example. However, it also relates to other radiation imaging modalities in which at least one of a radiation source and/or a detector array is rotated about an object under examination.

Today, CT and other radiation imaging modalities (e.g., mammography, digital radiography, etc.) are useful to provide information, or images, of interior aspects of an object under examination. Generally, the object is exposed to radiation (e.g., x-rays, gamma rays, etc.), and an image(s) is formed based upon the radiation absorbed and/or attenuated by the interior aspects of the object, or rather an amount of radiation photons that is able to pass through the object. Typically, highly dense aspects of the object absorb and/or attenuate more radiation than less dense aspects, and thus an aspect having a higher density, such as a bone or metal, for example, will be apparent when surrounded by less dense aspects, such as muscle or clothing.

Radiation imaging modalities generally comprise, among other things, one or more radiation sources (e.g., an x-ray source, Gamma-ray source, etc.) and a detector array comprised of a plurality of detector cells that are respectively configured to convert radiation that has traversed the object into signals that may be processed to produce the image(s). As an object is passed through an examination region defined between the radiation source(s) and the detector array, radiation is absorbed/attenuated by the object, causing changes in the amount of radiation detected by the detector array.

In some applications, the radiation source and the detector array are mounted on a single rotating unit, with the rotating unit rotating about the object as the object is passed through the rotating unit. The rotational speed of the rotating unit may be limited by, among other things, the size of the rotating unit, the weight of the detector array, and/or the weight of the radiation source. Moreover, in embodiments where an object is translated through the examination region during an examination, a speed of translation may be a function of the rotational speed of the rotating unit. Accordingly, throughput of the radiation imaging modality may be a function of, among other things, the rotational speed of the rotating unit.

SUMMARY

Aspects of the present application address the above matters, and others.

According to an aspect, a radiation system comprises a first rotating unit configured to rotate about a first axis of rotation, where the first rotating unit comprises a first radiation source configured to generate radiation within a first radiation spectrum. The radiation system comprises a second rotating unit configured to rotate about a second axis of rotation, where the second rotating unit comprises a detector array configured to detect at least a portion of the radiation generated by the first radiation source.

According to another aspect, a radiation system comprises a first rotating unit configured to rotate about a first axis of rotation, where the first rotating unit comprises a first radiation source configured to generate radiation. The radiation system comprises a second rotating unit configured to rotate about a second axis of rotation, where the second rotating unit comprises a detector array configured to detect at least a portion of the radiation generated by the first radiation source. The first rotating unit is configured to rotate asynchronously relative to the second rotating unit such that a relative position between the radiation source and the detector array is varied during an examination.

According to another aspect, a radiation system comprises a first rotating unit defining a first bore and configured to rotate about a first axis of rotation, where the first rotating unit comprises a first radiation source configured to generate radiation. The radiation system comprises a second rotating unit configured to be positioned within the first bore, the second rotating unit defining a second bore into which an object is positioned during an examination. The second rotating unit is configured to rotate about a second axis of rotation and comprises a detector array configured to detect at least a portion of the radiation generated by the first radiation source.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

Figure 1:
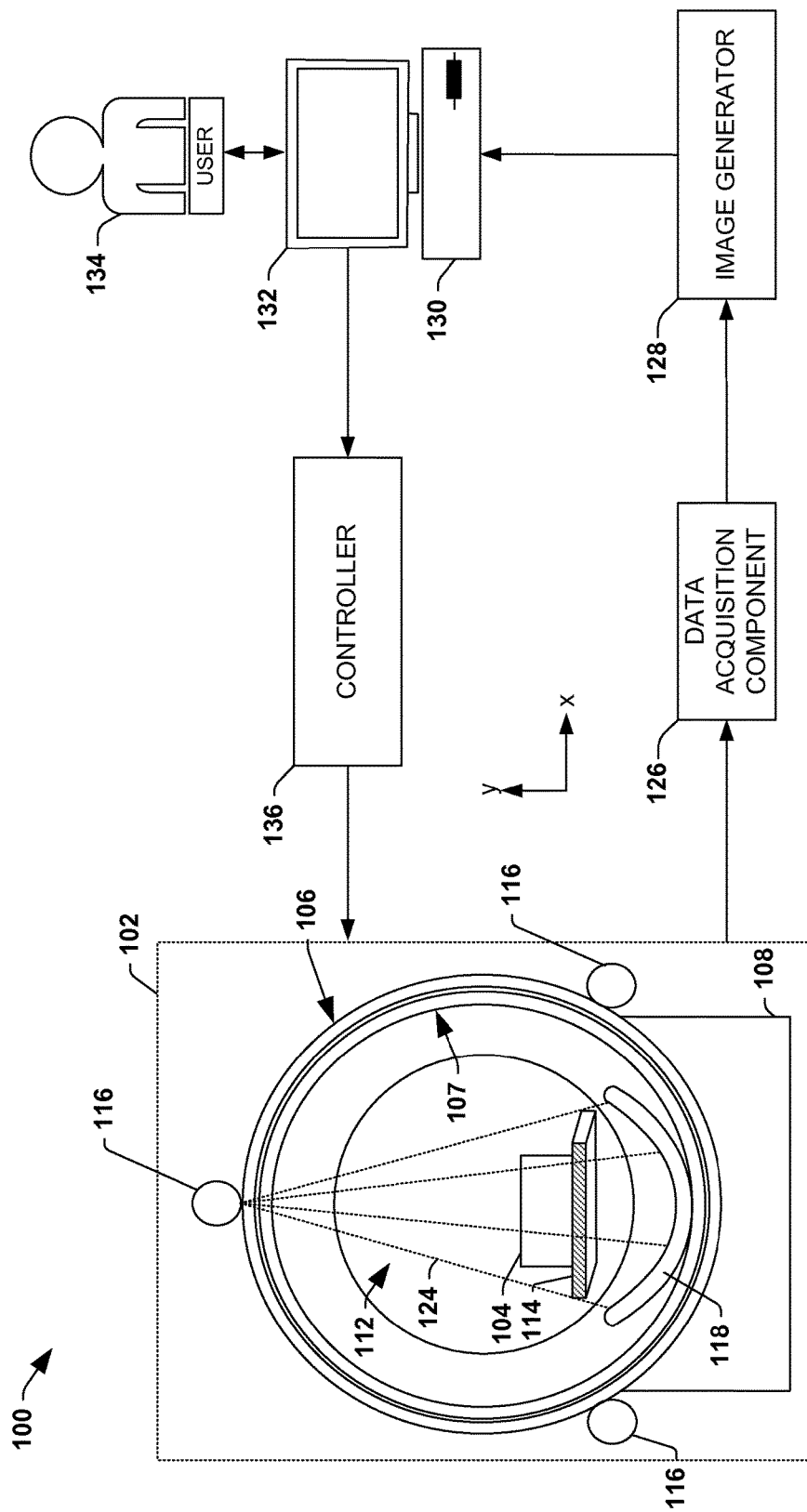
FIG. 1 illustrates an example environment of an imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Systems and/or techniques are provided to improve throughput of a radiation imaging system and/or to facilitate capturing a complete data set (e.g., representing a 360 degree view of an object) in less than the time it takes to complete a single revolution of a rotating gantry. One or more radiation sources are mounted to a first rotating unit while one or more detector arrays are mounted to a second rotating unit. In some embodiments, the first rotating unit and the second rotating unit are configured to rotate, such as about a common axis. During an examination of an object, a relative position between a detector array and a radiation source is varied such as by rotating the detector array asynchronously relative to the radiation source. For example, the first rotating unit may be rotated clockwise during an examination while the second rotating unit is rotated counter-clockwise. As another example, the first rotating unit and the second rotating unit may be rotated in a same direction, but at different rotational speeds.

In some embodiments, at least two radiation sources are mounted to a first rotating unit and are configured to illuminate the detector array at different times. For example, a first radiation source illuminates the detector array during a first period of time and the second radiation source illuminates the detector array at a second period of time, which may overlap or not overlap the second period of time. The first radiation source and the second radiation source may be configured to emit radiation at a same energy spectrum or at different energy spectra.

Referring to FIG. 1, a CT system 100 having at least one radiation source mounted to a different gantry than a detector array is provided. It is to be appreciated that while a CT system 100 is described herein, the instant application is not intended to be so limited. That is, to the extent practical, the instant application, including the scope of the claimed subject matter, is intended to be applicable to other systems that comprise a rotating unit having one or more electronic components and configured for movement relative to a unit, such as a stationary unit and/or a second rotating unit (e.g., which moves at a different speed and/or in a different direction than the rotating unit).

Moreover, it is to be appreciated that the example arrangement is not intended to be interpreted in a limiting manner, such as necessarily specifying the location, inclusion, and/or relative position of the components depicted therein. By way of example, in some embodiments, a data acquisition component 126 is part of a detector array 118.

An examination unit 102 of the CT system 100 is configured to examine objects 104 such as baggage, cargo, patients, etc. (e.g., where a cross-sectional view of the examination unit 102 is illustrated in FIG. 1). The examination unit 102 comprises a first rotating unit 106 and a second rotating unit 107. In the illustrated example, the second rotating unit 107 is positioned within the first rotating unit 106, such that the first rotating unit 106 extends concentrically around the second rotating unit 107. However, such a position of the first rotating unit 106 relative to the second rotating unit 107 is not intended to be limiting, and in other examples, the first rotating unit 106 may be positioned adjacent the second rotating unit 107.

The first rotating unit 106 and/or the second rotating unit 107 are configured to rotate relative to a stationary unit 108 in a rotational motion (e.g., rotating clockwise or counter-clockwise on the page). In some examples, the first rotating unit 106 and the second rotating unit 107 can rotate asynchronously, such as in a same or different direction and/or at a different rotational speed.

A bore 112, formed by the first rotating unit 106, defines a perimeter of an examination region in which objects 104 are examined. Objects 104 are translated through the examination region via a support article 114, such as a bed, conveyer belt, or roller system, for example.

The first rotating unit 106 comprises one or more radiation sources 116 (e.g., an ionizing radiation source such as an x-ray source or gamma-ray source). While three radiation sources 116 are illustrated in FIG. 1, in other examples, any number of radiation sources 116 (e.g., one or more) may be provided. Likewise, while the radiation sources 116 of FIG. 1 are spaced apart about 120° around the bore 112, in other examples, the radiation sources 116 may be positioned closer together (e.g., less than 120°), farther apart (e.g., greater than 120°), and/or may be positioned equidistant or non-equidistant from one another.

The second rotating unit 107 comprises one or more detector arrays 118. In the illustrated example, one of the radiation sources 116 is positioned above the bore 112 and the detector array 118 is positioned below the bore 112. It is to be appreciated that because the radiation sources 116 are mounted to the first rotating unit 106 while the detector array 118 is mounted to the second rotating unit 107, the relative positions between the radiation sources 116 and the detector array 118 may be varied during an examination. In some embodiments, the rotation of the first rotating unit 106 (and, thus, the radiation sources 116) and the rotation of the second rotating unit 107 (and, thus, the detector array 118) is in tandem with the translation of the object 104 (e.g., where the object is translated in a direction perpendicular to the x,y plane (e.g., sometimes referred to as the z-direction)) such that a helical examination is performed on the object 104. In other embodiments, the object 104 is not translated during the examination, and thus a helical examination is not performed despite the rotational motion of the first rotating unit 106 and the second rotating unit 107.

During an examination of the object 104, the radiation sources 116 can emit cone-beam and/or fan-beam shaped radiation 124 from a focal spot of the radiation source 116 (e.g., a region within the radiation source 116 from which radiation 124 emanates) into the examination region. For ease of illustration, FIG. 1 illustrates merely one of the radiation sources 116 emitting radiation 124, though, in other examples, some or all of the radiation sources 116 can emit radiation 124 in a similar manner concurrently and/or successively. The radiation 124 may be emitted substantially continuously and/or may be emitted intermittently (e.g., a brief pulse of radiation 124 emitted followed by a resting period during which the radiation source 116 is not activated). Further, the radiation 124 may be emitted at a single energy spectrum or multiple energy spectra.

As the emitted radiation 124 traverses the object 104, the radiation 124 may be absorbed and/or attenuated differently by different aspects of the object 104. Because different aspects absorb/attenuate different percentages of the radiation 124, the number of photons detected by respective detector cells of the detector array 118 may vary. For example, more dense aspects of the object(s) 104, such as a bone or metal plate, may attenuate more of the radiation 124 (e.g., causing fewer photons to impinge a region of the detector array 118 shadowed by the more dense aspects) than less dense aspects, such as skin or clothing.

Radiation detected by the detector array 118 may be directly or indirectly converted into analog signals that can be transmitted from the detector array 118 to a data acquisition component 126 operably coupled to the detector array 118. The analog signal(s) may carry information indicative of the radiation detected by the detector array 118. The information that can be derived from the analog signal may be a function of whether the detector array 118 is an integrating-type detector array (e.g., configured to integrate charge over a sampling period) and/or a photon counting type detector array (e.g., configured to count detection events and/or determine the energy of respective radiation photons).

The data acquisition component 126 is configured to convert the analog signals output by the detector array 118 into digital signals and/or to compile signals that were transmitted within a predetermined time interval, or measurement interval, using various techniques (e.g., integration, photon counting, etc.). The compiled signals are typically in projection space and are, at times, referred to as projections.

The projections and/or digital signals generated by the data acquisition component 126 may be transmitted to an image generator 128 (e.g., at times referred to as an image reconstructor) configured to convert the data from projection space to image space using suitable analytical, iterative, and/or other reconstruction techniques (e.g., tomosynthesis reconstruction, back-projection, iterative reconstruction, etc.). Such images may depict a two dimensional representation of the object 104 and/or a three dimensional representation of the object 104, for example. In other embodiments, the projections and/or digital signals may be transmitted to other processing components, such as a threat analysis component, for processing.

The example CT system also includes a terminal 130, or workstation (e.g., a computer), configured to receive image(s) from the image generator 128, which can be displayed on a monitor 132 to a user 134 (e.g., security personnel, medical personnel, etc.). In this way, the user 134 can inspect the image(s) to identify areas of interest within the object(s) 104. The terminal 130 can also be configured to receive user input, which can direct operations of the examination unit 102 (e.g., a speed of rotation, an energy level of the radiation 124, a desired voltage applied to the radiation sources 116, etc.).

In the example environment, a controller 136 is operably coupled to the terminal 130. The controller 136 may be configured to control operations of the examination unit 102, for example. By way of example, in some embodiments, the controller 136 may be configured to receive information from the terminal 130 and to issue instructions to the examination unit 102 indicative of the received information (e.g., adjust a speed of a conveyor belt, adjust a relative rotational speed between the first rotating unit 106 and the second rotating unit 107, etc.).

Figure 2A:
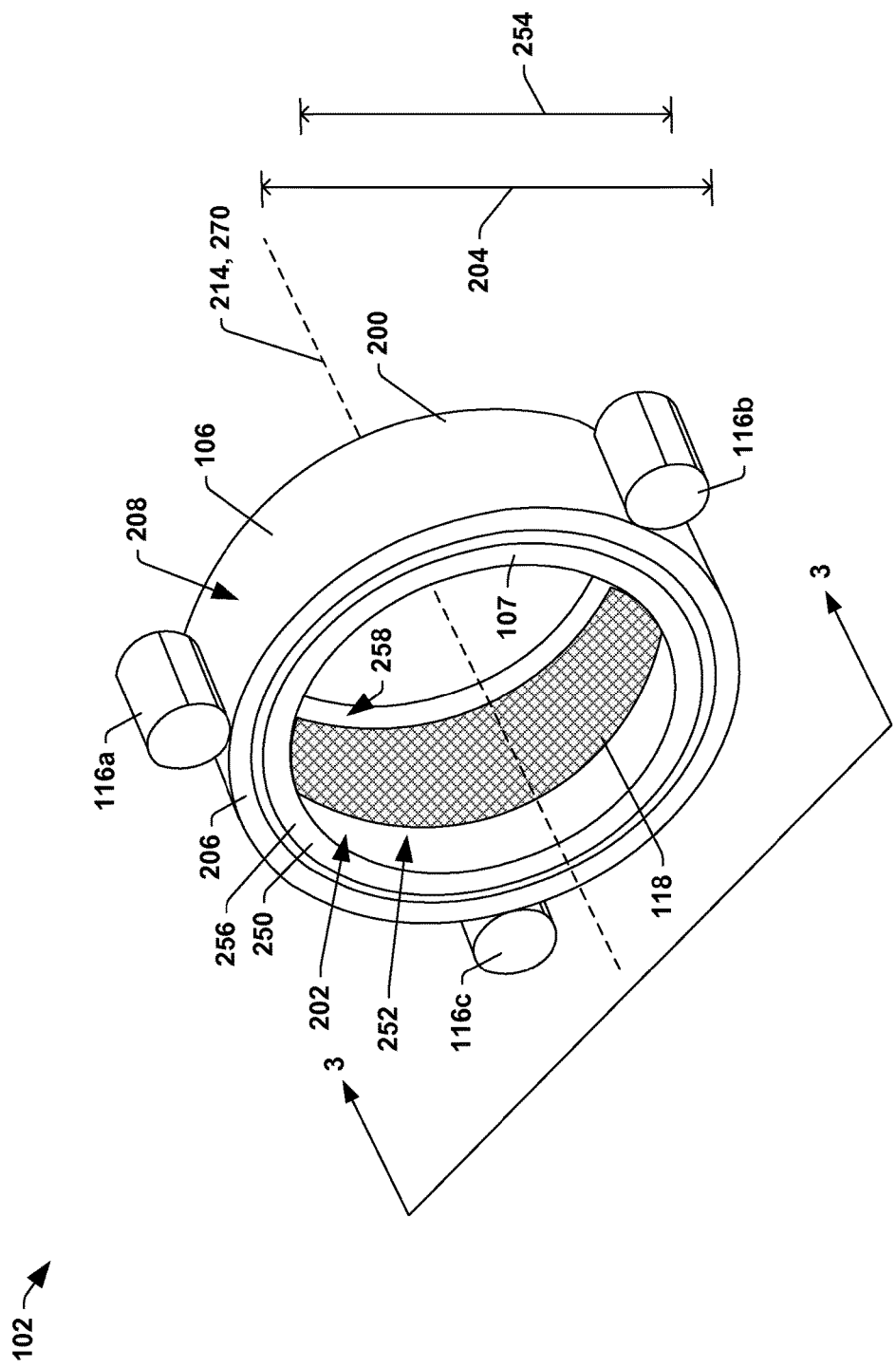
FIG. 2a illustrates a perspective view of an example examination unit.
Figure 2B:
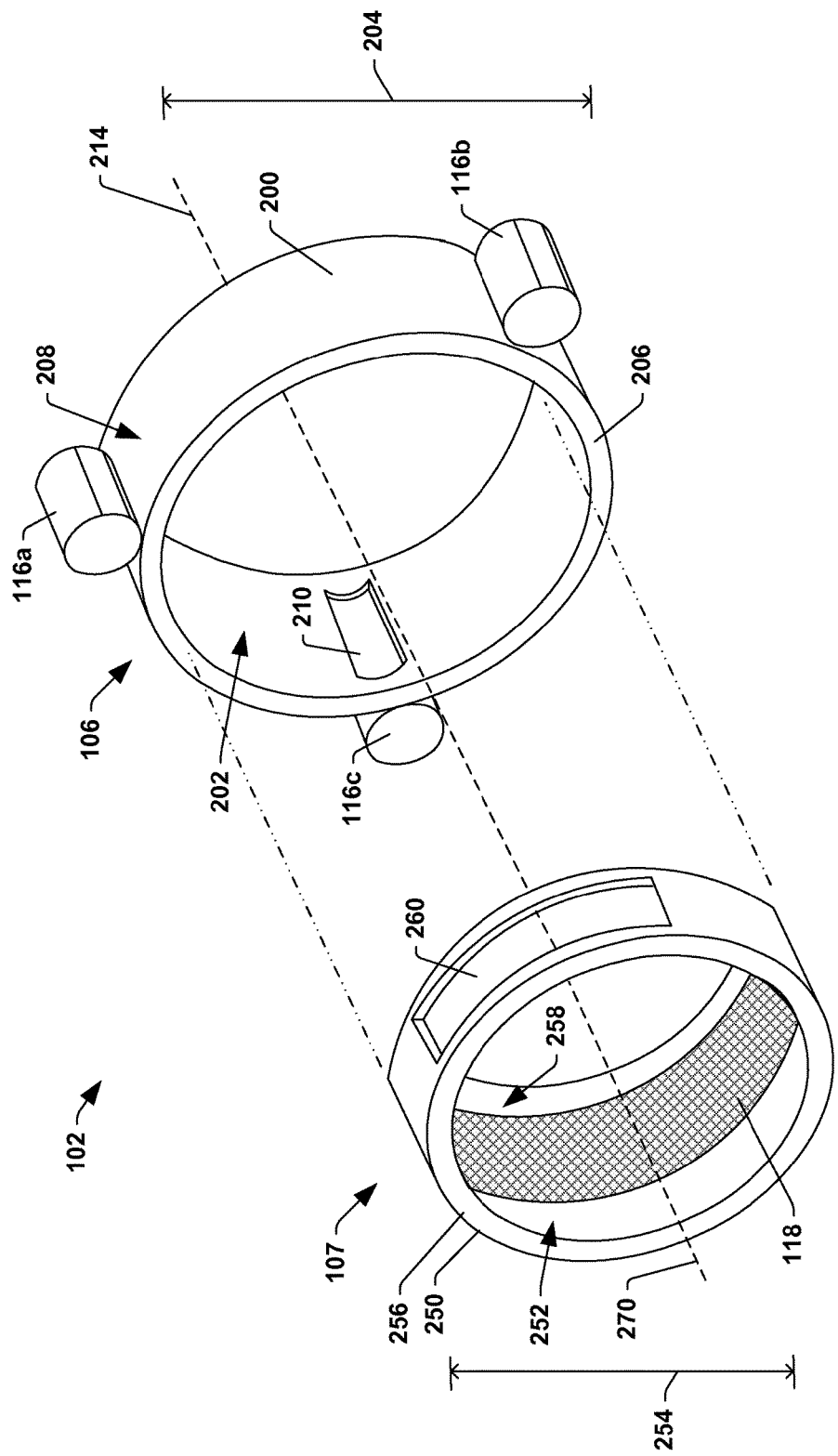
FIG. 2b illustrates a partially exploded perspective view of an example examination unit.

FIGS. 2a and 2b illustrate a perspective view of the examination unit 102, according to some embodiments. The examination unit 102 comprises the first rotating unit 106. The first rotating unit 106 can rotate relative to the stationary unit 108 (illustrated in FIG. 1) in a rotational motion (e.g., rotating clockwise or counter-clockwise on the page). Any number of structures can be provided to allow for rotational motion of the first rotating unit 106, including, but not limited to, rotators, belts, chains, gear systems, drive units, pulleys, etc.

The first rotating unit 106 may include a first drum 200. In an example, the first drum 200 has a generally cylindrical geometry (e.g., or a right circular cylinder). The first drum 200 of the first rotating unit 106 defines a first bore 202 having a first diameter 204. The first drum 200 comprises any number of sizes. In one possible example, the first drum 200 has an outer diameter of about 4 feet (~1.2 meters) to about 5 feet (~1.5 meters). In such an example, the first drum 200 may include a first sidewall 206 that defines the first bore 202, with the first sidewall 206 having a thickness of about 2 inches (~5.1 cm) to about 3 inches (~7.6 cm). As such, the first bore 202 may have a diameter that is a few inches smaller than the outer diameter of the first drum 200. It will be appreciated that the dimensions stated herein are merely example dimensions, such that the disclosure is not limited to these dimensions.

The first drum 200 of the first rotating unit 106 is not limited to the circular shape, as illustrated. Rather, other geometries are envisioned. For example, the first drum 200 may have an ovoid/elliptical shape, quadrilateral (e.g., square, rectangular, etc.), shape, triangular shape, etc. Indeed, in the illustrated example, the first drum 200 may not comprise a perfectly circular shape.

The first rotating unit 106 comprises a first radiation source 116a, a second radiation source 116b, and a third radiation source 116c. While three radiation sources 116a to 116c are illustrated in FIGS. 2a and 2b, any number (e.g., one or more) of radiation sources may be provided. In this example, the radiation sources 116 are spaced approximately equidistant apart (e.g., spaced about 120°) around an outer surface 208 of the first drum 200. Such a position is not intended to be limiting, however, and in other examples, the radiation sources 116 can be positioned closer together, farther apart and/or non-equidistant from one another.

The first radiation source 116a can generate radiation within a first radiation spectrum. The second radiation source 116b can generate radiation within a second radiation spectrum. In some examples, the first radiation spectrum is substantially equal to the second radiation spectrum. The third radiation source 116c can generate radiation within a third radiation spectrum. In some examples, the second radiation spectrum is substantially equal to the third radiation spectrum. In some examples, the first radiation spectrum is substantially equal to the third radiation spectrum.

The first sidewall 206 of the first drum 200 can define one or more openings 210 (illustrated in FIG. 2b) extending through the first sidewall 206 (e.g., radially through). It will be appreciated that while merely one opening is illustrated in FIG. 2b, any number of openings is contemplated. In general, the openings 210 (e.g., apertures, windows, spaces, etc.) are positioned to accommodate/match a location of the radiation sources 116. For example, depending on the composition of the first drum 200, radiation from the radiation sources 116 may be absorbed and/or attenuated by the first drum 200 if the radiation passes through the first sidewall 206. As such, the first drum 200 defines the openings 210 through which the radiation, emitted from the radiation sources 116, may pass (e.g., unattenuated) to enter the first bore 202.

It will be appreciated that the need for the openings 210 may depend upon, among other things, the location of the radiation sources 116, the location of the detector array 118, and/or the composition of the first drum 200 (e.g., the first sidewall 206). In some examples, the openings 210 may be unnecessary due to the positioning of the radiation sources 116 with respect to the detector array 118. In one possible example, the first drum 200 may include a radiation transparent material (e.g., a material that absorbs and/or attenuates little, if any, radiation, such as plastics), such that the openings 210 may be unnecessary. Conversely, if the first drum 200 is comprised of a radiation opaque material, such as a metal material, for example, one or more of the openings 210 for radiation passage may be desirable to mitigate attenuation by the first sidewall 206 if the radiation sources 116 are mounted outside of the first bore 202, as illustrated.

The first drum 200 of the first rotating unit 106 comprises any number of constructions. For example, the first drum 200 may define a generally smooth inner surface. Moreover, the first drum 200 may comprise a single-piece (e.g., unibody) formed structure. In other possible examples, a plurality of portions/segments may be fastened/secured/attached together to form the first drum 200. In an example, the first drum 200 may include a single-piece metal structure, though in other examples, the first drum 200 may include plastic materials, metal and plastic materials, etc.

The first rotating unit 106 can rotate about a first axis of rotation 214. In some examples, the first rotating unit 106 rotates about the first axis of rotation 214 in a clockwise direction. In other examples, the first rotating unit 106 rotates about the first axis of rotation 214 in a counter-clockwise direction. The first rotating unit 106 can rotate about the first axis of rotation 214 at any number of rotational speeds and, in some examples, may have a varying rotational speed.

Referring still to FIGS. 2a and 2b, the examination unit 102 comprises the second rotating unit 107. The second rotating unit 107 can rotate relative to the stationary unit 108 in a rotational motion (e.g., rotating clockwise or counter-clockwise on the page). Any number of structures can be provided to allow for rotational motion of the second rotating unit 107, including, but not limited to, rotators, belts, chains, gear systems, drive units, pulleys, etc.

The second rotating unit 107 may include a second drum 250. In an example, the second drum 250 has a generally cylindrical geometry (e.g., or a right circular cylinder). The second drum 250 of the second rotating unit 107 defines a second bore 252 having a second diameter 254. The second drum 250 comprises any number of sizes. In some examples, the second diameter 254 of the second bore 252 is different than the first diameter 204 of the first bore 202 of the first drum 200. In an example, the first diameter 204 is greater than the second diameter 254. The second drum 250 may include a second sidewall 256 that defines the second bore 252. The second drum 250 comprises any number of materials, including metals, composite materials (e.g., carbon fiber composites), air bearings, magnetic bearings, etc.

The second drum 250 of the second rotating unit 107 is not limited to the circular shape, as illustrated. Rather, other geometries are envisioned. For example, the second drum 250 may have an ovoid/elliptical shape, quadrilateral (e.g., square, rectangular, etc.) shape, triangular shape, etc. Indeed, in the illustrated example, the second drum 250 may not comprise a perfectly circular shape. In some examples, the second drum 250 may have a substantially matching shape to the first drum 200. In the illustrated example, the second diameter 254 of the second bore 252 of the second drum 250 is less than the first diameter 204 of the first bore 202 of the first drum 200, such that the second drum 250 can be received within the first bore 202 of the first drum 200. In an example, the first diameter 204 of the first bore 202 of the first drum 200 is sufficiently large enough to receive the second drum 250 therein without the second drum 250 contacting the first drum 200.

The second rotating unit 107 comprises the detector array 118. The detector array 118 may be supported along an inner surface 258 of the second sidewall 256. In a possible example, the detector array 118 is positioned on and/or attached to the inner surface 258. In another possible example, the detector array 118 may be positioned within an opening, aperture, window, or the like that extends into and/or through the second sidewall 256. In yet another possible example, the detector array 118 may be positioned on and/or attached to an outer surface of the second drum 250, with the detector array 118 aligned with an opening, window, or the like defined within the second sidewall 256.

The detector array 118 is not limited to the illustrated dimensions of FIGS. 2a and 2b. Rather, the detector array 118 may have a larger or smaller size, such as by being wider or narrower and/or by extending a longer or shorter distance circumferentially around the second drum 250. In some examples, the detector array 118 may extend about ⅓ (e.g., about 120°) around the second drum 250, ⅔ (e.g., about 240°) around the second drum 250, etc.

As illustrated in FIG. 2b, the second rotating unit 107 comprises an aperture 260 that extends through the second sidewall 256 of the second drum 250 (e.g., radially through). It will be appreciated that while merely one opening is illustrated in FIG. 2b, any number of apertures 260 (e.g., one or more) may be provided. In general, the aperture 260 (e.g., openings, windows, spaces, etc.) is positioned substantially diametrically opposed from the detector array 118. Radiation from the radiation sources 116a-116c may pass through the aperture 260 so as to be received by the detector array 118.

The aperture 260 comprises any number of sizes. In some examples, the aperture 260 extends between about 45° to about 90° around the second drum 250. In other examples, however, the aperture 260 may have a longer circumferential length, such as by extending greater than about 90° around the second drum 250, or may have a shorter circumferential length, such as by extending less than about 45° around the second drum 250. In some examples, the aperture 260 and the detector array 118 may, together, extend around substantially the entire second drum 250. For example, the aperture 260 may extend around about ⅓ (e.g., about 120°) of the second drum 250 while the detector array 118 may extend around about the remaining ⅔ (e.g., about 240°) of the second drum 250.

The second drum 250 is not limited to including the aperture 260. Rather, in other examples, at least a portion of the second drum 250 may include a material that is radiation transparent (e.g., a material that absorbs and/or attenuates little, if any, radiation, such as plastics). In such an example, the radiation transparent material may be disposed substantially diametrically opposed from the detector array 118, such as at the location where the aperture 260 is positioned in FIG. 2b.

The detector array 118 is substantially diametrically opposed from the aperture 260 such that the detector array 118 can detect at least a portion of the radiation 124 (illustrated in FIG. 1) generated by the radiation sources 116. For example, the detector array 118 can detect at least a portion of the radiation 124 generated by the first radiation source 116a when the first radiation source 116a is visible through the window 260. In another example, the detector array 118 can detect at least a portion of the radiation 124 generated by the second radiation source 116b when the second radiation source 116b is visible through the window 260. In another example, the detector array 118 can detect at least a portion of the radiation 124 generated by the third radiation source 116c when the third radiation source 116c is visible through the window 260.

The second rotating unit 107 can rotate about a second axis of rotation 270. In some examples, the second axis of rotation 270 is coaxial with respect to the first axis of rotation 214. As such, the first rotating unit 106 may be coaxial with respect to the second rotating unit 107. In other examples, however, the first axis of rotation 214 and the second axis of rotation 270 may not be coaxial. Rather, the first axis of rotation 214 and the second axis of rotation 270 may be parallel or non-parallel to one another.

The second rotating unit 107 may rotate about the second axis of rotation 270 in a clockwise direction or in a counter-clockwise direction. The second rotating unit 107 can rotate about the second axis of rotation 270 at any number of rotational speeds. In an example, the first rotating unit 106 and the second rotating unit 107 can rotate in the same direction, such as by rotating clockwise together or counter-clockwise together. In other examples, the first rotating unit 106 and the second rotating unit 107 can rotate in opposite directions. In such an example, the first rotating unit 106 may rotate in the clockwise direction while the second rotating unit 107 may rotate in the counter-clockwise direction. Alternatively, the first rotating unit 106 may rotate in the counter-clockwise direction while the second rotating unit 107 may rotate in the clockwise direction. The first rotating unit 106 and the second rotating unit 107 can rotate at substantially the same speed, or, in other examples, at different speeds.

Turning to FIGS. 3a to 3e, an example examination is illustrated as seen from a perspective indicated by lines 3-3 in FIG. 2a. During the examination, the first rotating unit 106 can rotate asynchronously relative to the second rotating unit 107 such that a relative position between the first radiation source 116a and the detector array 118 may be varied during the examination. Similarly, due to this asynchronous rotation between the first rotating unit 106 and the second rotating unit 107, a relative position between the second radiation source 116b and the detector array 118 may be varied during the examination. Likewise, due to this asynchronous rotation between the first rotating unit 106 and the second rotating unit 107, a relative position between the third radiation source 116c and the detector array 118 may be varied during the examination.

In an example, by rotating asynchronously, the first rotating unit 106 may rotate at a different rotational speed than the second rotating unit 107. For example, the first rotating unit 106 may rotate at a faster or slower rotational speed than the second rotating unit 107. Additionally or alternatively, by rotating asynchronously, the first rotating unit 106 may rotate in an opposite rotational direction (e.g., clockwise or counter-clockwise) than a rotational direction of the second rotating unit 107.

Figure 3A:
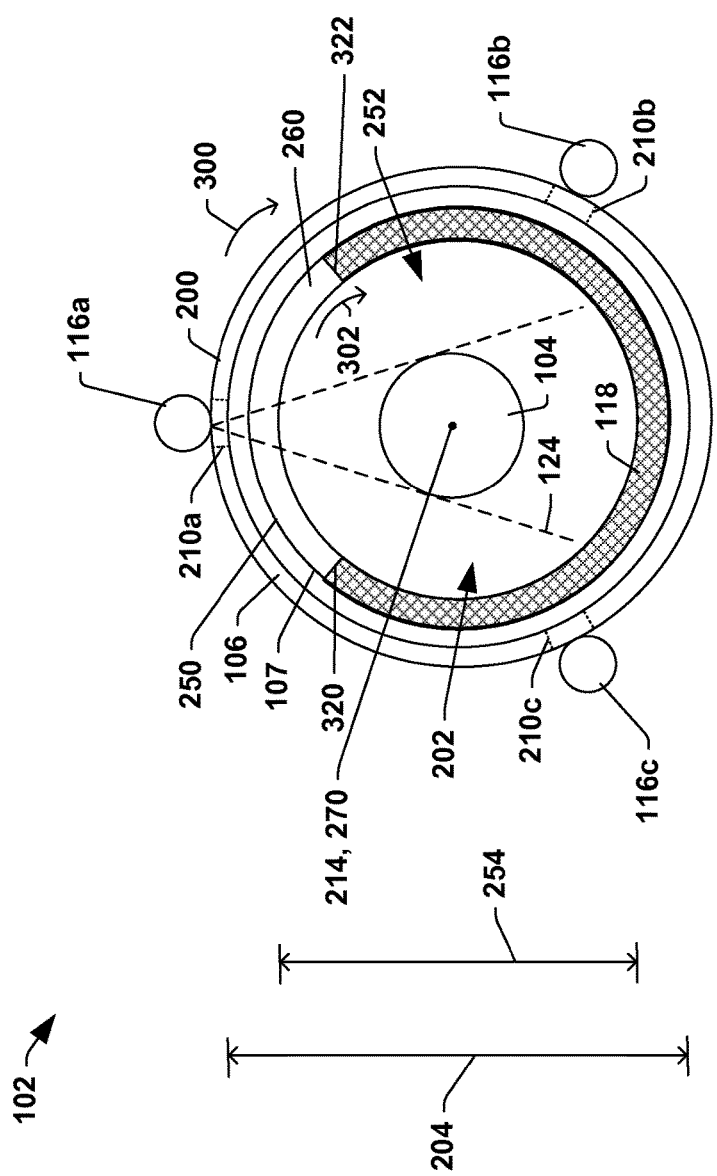
FIG. 3a illustrates a side view of an example examination unit.

Referring to FIG. 3a, a first portion of the examination is illustrated. In this example, the detector array 118 is sub-stantially diametrically opposite from the first radiation source 116a such that the first radiation source 116a illuminates the detector array 118 during the first portion of the examination. Though not illustrated in this example, one or more of the objects 104 (illustrated in FIG. 1) may be disposed within the examination unit 102 (e.g., within the first bore 202 and the second bore 252). In this example, the radiation 124 can pass through the opening 210 (e.g., a first opening 210a) in the first drum 200 and through the aperture 260 (illustrated between the dashed/broken lines) in the second drum 250. The radiation 124 can pass through the object 104 and may be absorbed and/or attenuated differently by different aspects of the object 104. The radiation 124 passing through the object 104 may then be received by the detector array 118.

In the illustrated example, the first rotating unit 106 and the second rotating unit 107 can rotate in the same direction (e.g., clockwise). In other possible examples, however, the first rotating unit 106 may rotate in the opposite rotational direction (e.g., clockwise or counter-clockwise) than the second rotating unit 107. The first rotating unit 106 can rotate about the first axis of rotation 214 at a first rotational speed 300. In such an example, the second rotating unit 107 can rotate about the second axis of rotation 270 at a second rotational speed 302. In some examples, the first rotational speed 300 is different than the second rotational speed 302. For example, the first rotational speed 300 may be less than the second rotational speed 302. That is, the first rotating unit 106 and the second rotating unit 107 may complete a different number of rotations, revolutions, cycles, turns, etc. about the axes of rotation (e.g., first axis of rotation 214 and second axis of rotation 270) over a period of time.

The detector array 118 extends between a first edge 320 and a second edge 322. In the illustrated example, due to the second rotating unit 107 rotating in a clockwise direction, the first edge 320 is the leading edge while the second edge 322 is the trailing edge. However, in examples in which the second rotating unit 107 rotates in the counter-clockwise direction, the first edge 320 may be the trailing edge while the second edge 322 is the leading edge. In the illustrated example, during the first portion of the examination, a leading edge and a trailing edge of the radiation 124 from the first radiation source 116a can be directed between the first edge 320 and the second edge 322 of the detector array 118.

Figure 3B:
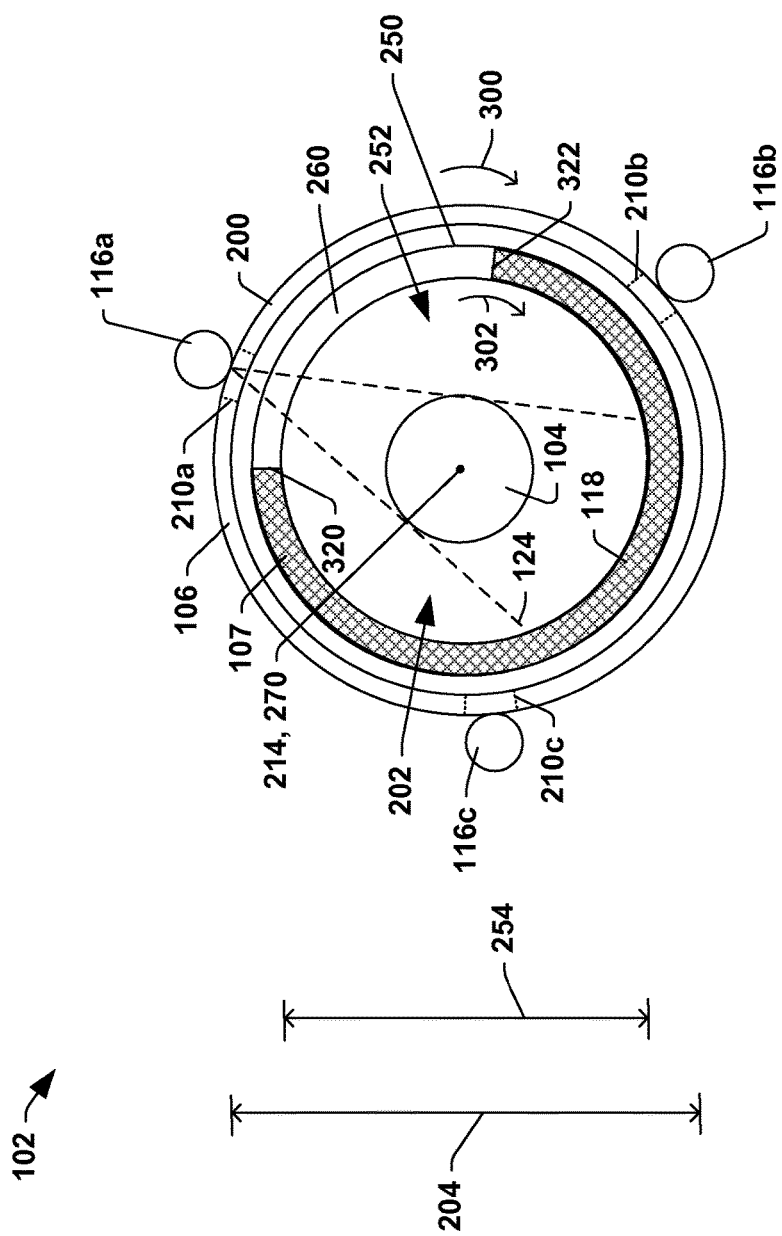
FIG. 3b illustrates a side view of an example examination unit.

Turning to FIG. 3b, the first portion of the examination is illustrated a period of time after the example of FIG. 3a. In the illustrated example, the first rotating unit 106 is rotating at the first rotational speed 300 while the second rotating unit 107 is rotating at the second rotational speed 302. Due to the first rotational speed 300 being less than the second rotational speed 302 in this example, the second rotating unit 107 rotates about the axis (e.g., the second axis of rotation 270) a greater distance than the first rotating unit 106 rotates about the axis (e.g., the first axis of rotation 214) over a period of time.

In this example, the radiation 124 from the first radiation source 116a continues to pass through the first opening 210a of the first rotating unit 106 and through the aperture 260 of the second rotating unit 107. This radiation 124 may be received by the detector array 118.

Figure 3C:
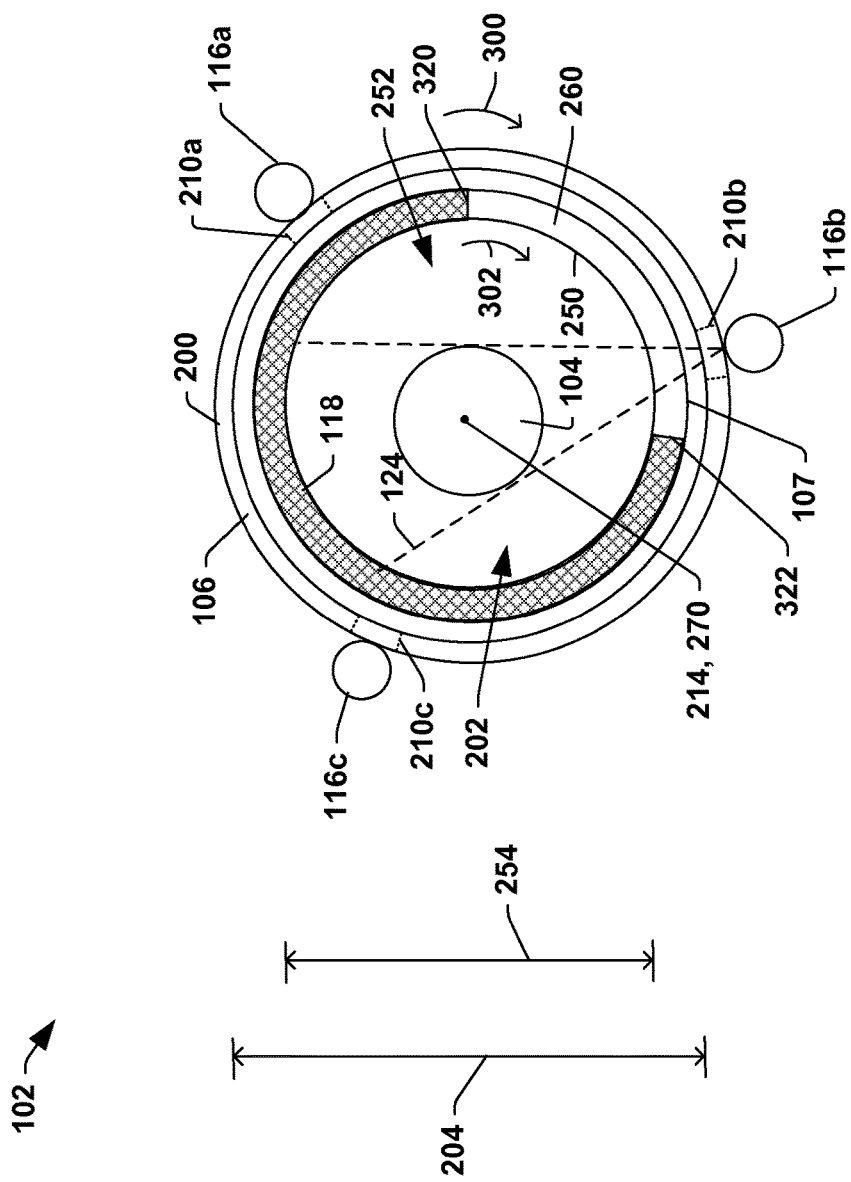
FIG. 3c illustrates a side view of an example examination unit.

Turning to FIG. 3c, a second portion of the examination is illustrated after the first portion of the examination. In this example, due to the first rotational speed 300 being less than the second rotational speed 302, the second rotating unit 107 rotates about the second axis of rotation 270 a greater distance than the first rotating unit 106 rotates about the first axis of rotation 214. In such an example, the radiation 124 from the first radiation source 116a may no longer be received by the detector array 118. That is, the aperture 260 is no longer aligned with the first radiation source 116a during the second portion of the examination. As such, in some examples, the first radiation source 116a may be turned off. In other examples, the first radiation source 116a may remain on though the radiation 124 emitted/generated by the first radiation source 116a is generally blocked by the second drum 250.

In this example, the radiation 124 may be generated by and emitted from the second radiation source 116b. The aperture 260 of the second rotating unit 107 may be aligned with the second radiation source 116b during this second portion of the examination. As such, the radiation 124 may pass through the second opening 210b of the first rotating unit 106 and through the aperture 260 of the second rotating unit 107. The radiation 124 can pass through the object 104 and may be absorbed and/or attenuated differently by different aspects of the object 104. The radiation 124 passing through the object 104 may then be received by the detector array 118.

Figure 3D:
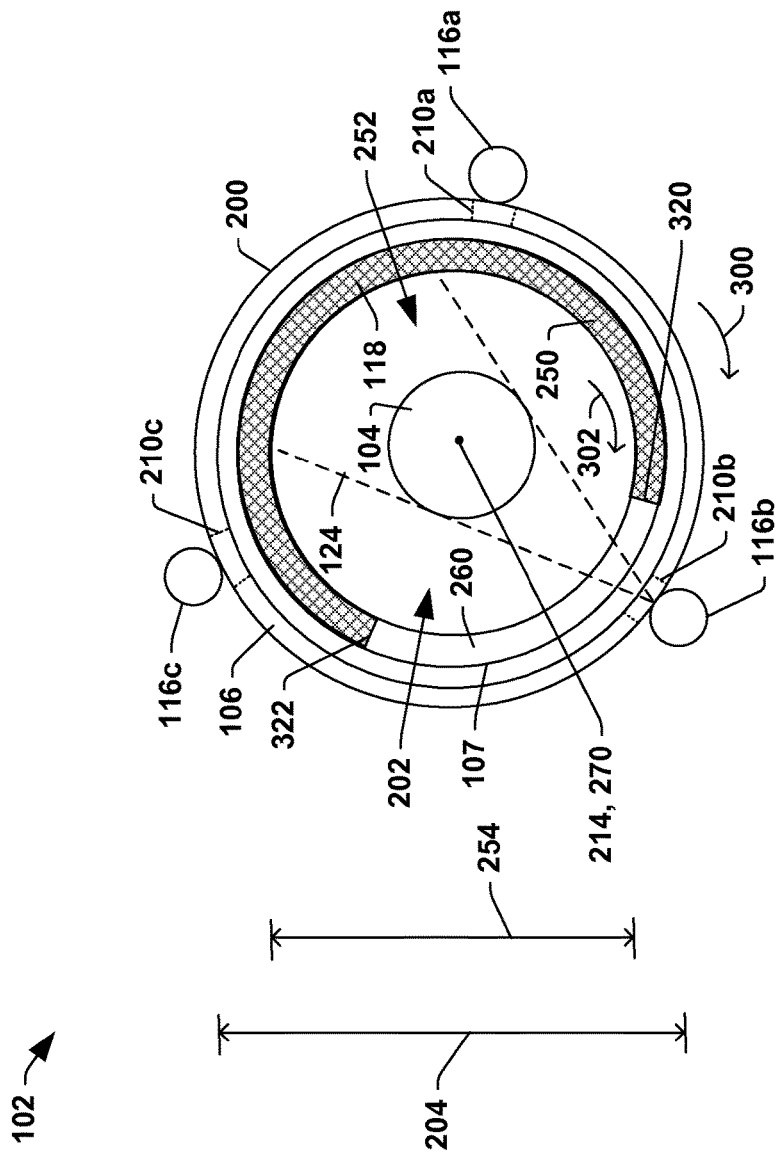
FIG. 3d illustrates a side view of an example examination unit.

Turning to FIG. 3d, the second portion of the examination is illustrated a period of time after the example of FIG. 3c. In the illustrated example, the radiation 124 from the second radiation source 116b continues to pass through the second opening 210b of the first rotating unit 106 and through the aperture 260 of the second rotating unit 107. This radiation 124 may be received by the detector array 118.

Figure 3E:
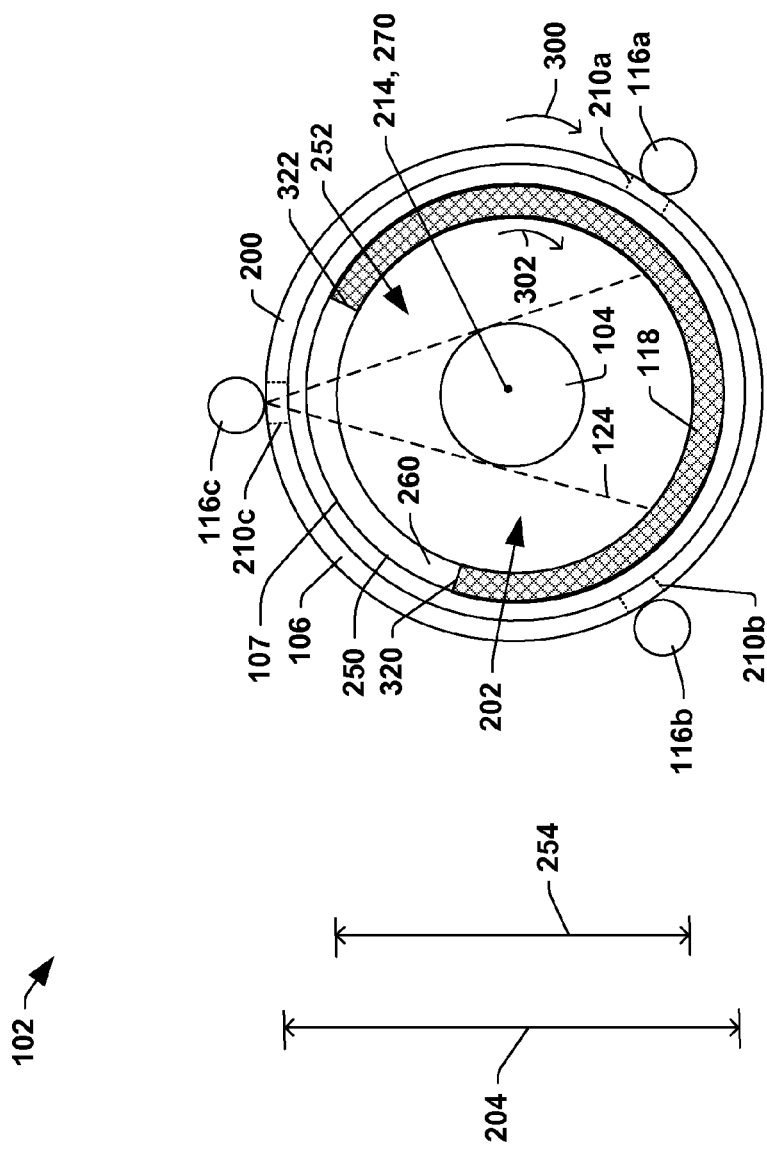
FIG. 3e illustrates a side view of an example examination unit.

Turning to FIG. 3e, a third portion of the examination is illustrated a period of time after the example of FIG. 3d. In the illustrated example, the radiation 124 from the second radiation source 116b may no longer be received by the detector array 118. That is, the aperture 260 is no longer aligned with the second radiation source 116b during the third portion of the examination such that the radiation 124 may not pass from the second radiation source 116b through the aperture 260. In some examples, the second radiation source 116b may be turned off during this third portion of the examination. In other examples, the second radiation source 116b may remain on though the radiation 124 emitted/generated by the second radiation source 116b is generally blocked by the second drum 250.

In this example, the radiation 124 may be generated by and emitted from the third radiation source 116c. The aperture 260 of the second rotating unit 107 is aligned with the third radiation source 116c during this third portion of the examination. As such, the radiation 124 may pass through a third opening 210c of the first rotating unit 106 and through the aperture 260 of the second rotating unit 107. The radiation 124 passing through the object 104 may then be received by the detector array 118.

Figure 4:
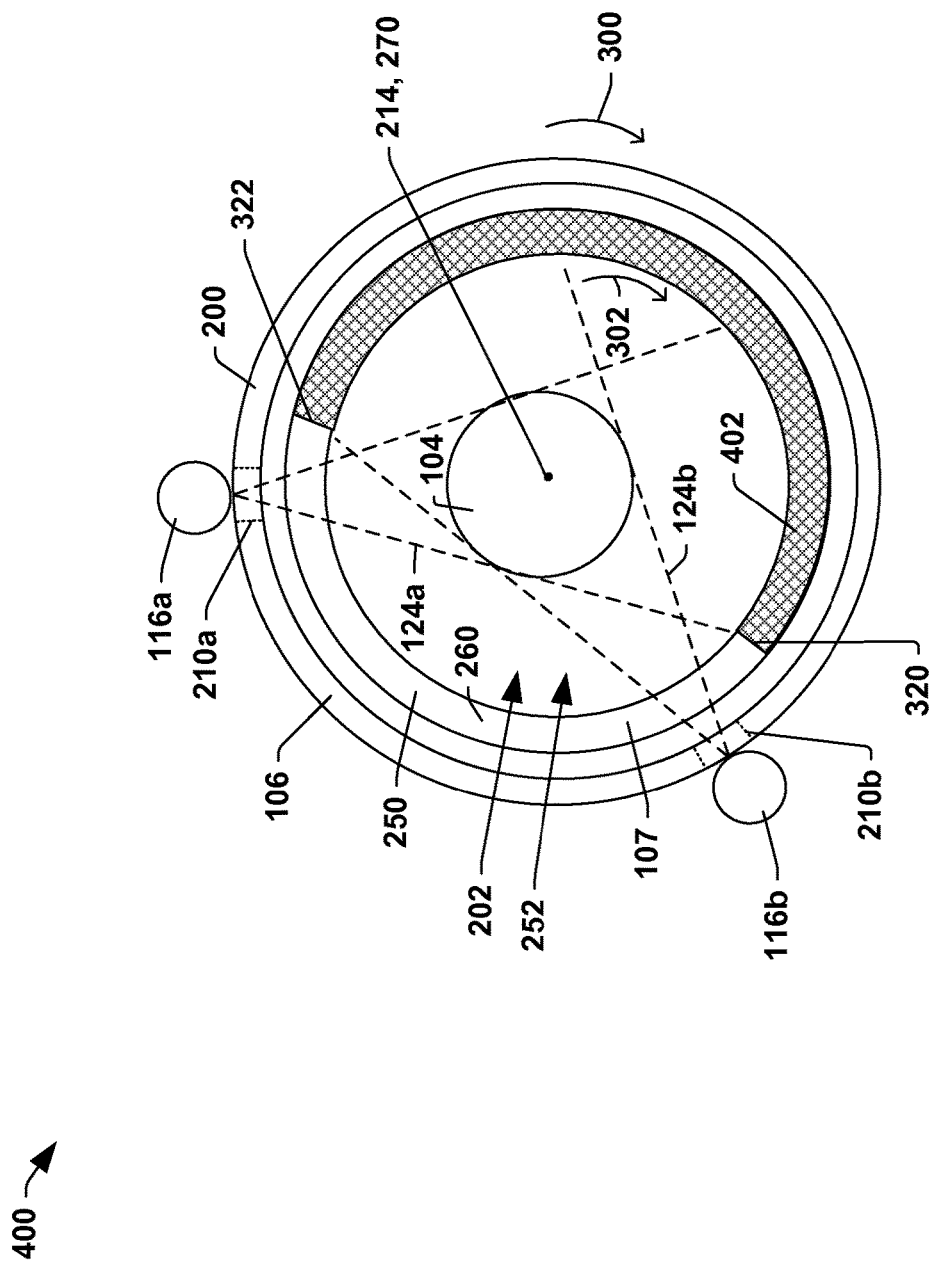
FIG. 4 illustrates a side view of an example examination unit.

Turning to FIG. 4, an example of a second examination unit 400 is illustrated. The second examination unit 400 may include at least some features of the examination unit 102 described with respect to FIGS. 1 to 3. For example, the second examination unit 400 may include the first rotating unit 106, the second rotating unit 107, the first drum 200, the second drum 250, etc.

In the illustrated example, the first rotating unit 106 may include the first radiation source 116a and the second radiation source 116b. While any number of radiation sources may be provided, at least in this example, the first rotating unit 106 may not include the third radiation source 116c. The first radiation source 116a and the second radiation source 116b can be spaced apart between about 110° to about 130° around the first drum 200.

The second rotating unit 107 may include a detector array 402. In this example, the detector array 402 may have a longer length (e.g., circumferential length) or shorter length than the detector array 118 illustrated in FIGS. 1 to 3. In this example, the detector array 402 may extend circumferentially around the second drum 250 between about 180° to about 270°. In some embodiments, the aperture 260 may extend circumferentially around the second drum 250 between about 90° to about 180°.

As with the previously described examination unit 102, the first rotating unit 106 and the second rotating unit 107 can rotate about the first axis of rotation 214 and the second axis of rotation 270, respectively. For example, the first rotating unit 106 can rotate about the first axis of rotation 214 at the first rotational speed 300. The second rotating unit 107 can rotate about the second axis of rotation 270 at the second rotational speed 302. In this example, the first rotational speed 300 is substantially equal to the second rotational speed. That is, the first rotating unit 106 and the second rotating unit 107 may complete the same number of rotations, revolutions, cycles, turns, etc. about the axes of rotation (e.g., first axis of rotation 214 and second axis of rotation 270) over a given period of time despite having a different tangential speed (e.g., linear speed along a circular path).

By rotating at substantially the same rotational speed in the same direction (e.g., clockwise or counter-clockwise), the detector array 402 can simultaneously receive first radiation 124a from the first radiation source 116a and second radiation 124b from the second radiation source 116b. For example, a leading edge of the first radiation 124a can be generally aligned with the first edge 320 of the detector array 402. As such, at least a portion of the first radiation 124a may be received by the detector array 402 while the first rotating unit 106 and the second rotating unit 107 rotate. In this example, a trailing edge of the second radiation 124b can be generally aligned with the second edge 322 of the detector array 402. As such, at least a portion of the second radiation 124b may be received by the detector array 402 while the first rotating unit 106 and the second rotating unit 107 rotate.

In this example, both the first radiation source 116a and the second radiation source 116b may be active at the same time. As such, the detector array 402 may simultaneously receive at least a portion of the first radiation 124a from the first radiation source 116a and at least a portion of the second radiation 124b from the second radiation source 116b. In some embodiments, to distinguish radiation events (e.g., detected photons) corresponding to the first radiation source 116a from radiation events corresponding to the second radiation source 116b, the first radiation source 116a may be configured to emit radiation at a different energy spectrum than the second radiation source 116b (e.g., where the energy spectrum emitted by the first radiation source 116a does not overlap the energy spectrum emitted by the second radiation source 116b). In still other embodiments, radiation events may be distinguished based upon the location on the detector array 402 where the event occurred (e.g., because respective radiation sources are illuminating different, non-overlapping portions of the detector array 402). Accordingly, coverage and speed of the second examination unit 400 is improved.

Figure 5A:
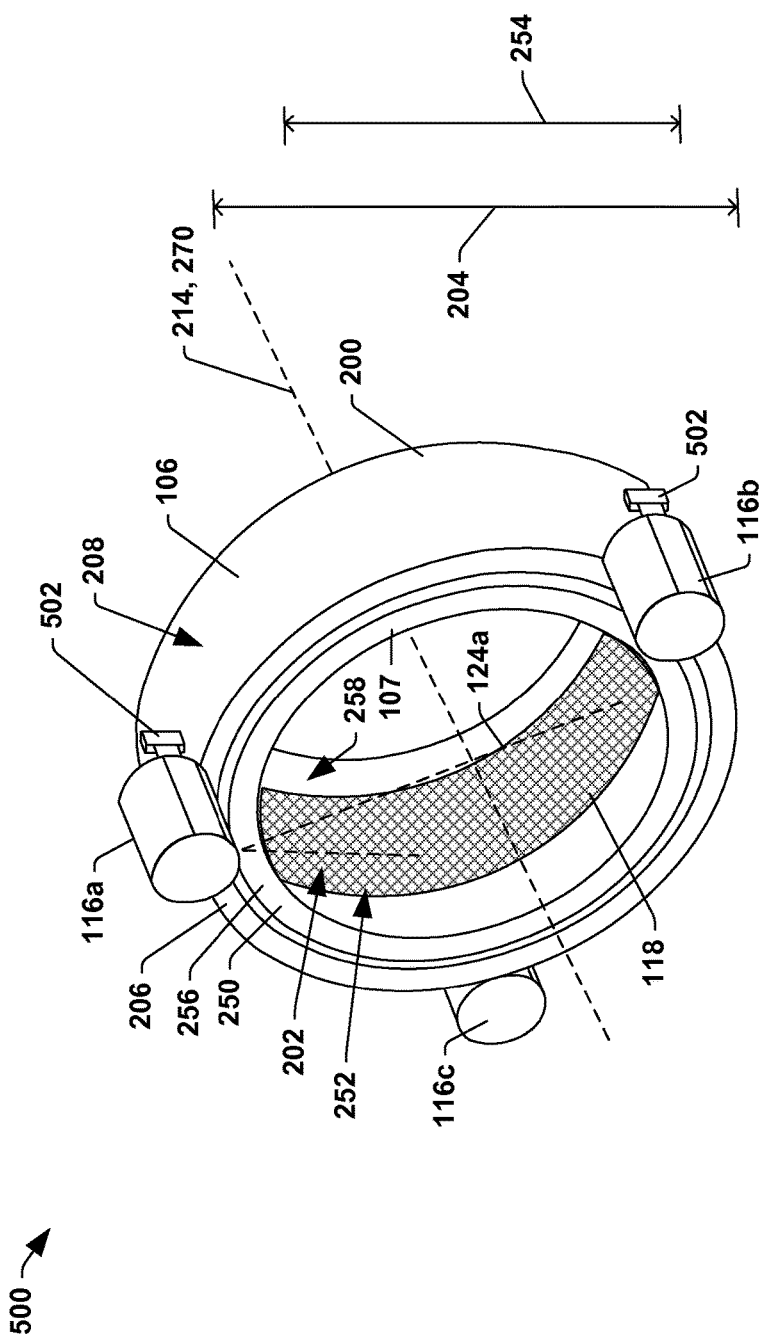
FIG. 5a illustrates a perspective view of an example examination unit.
Figure 5B:
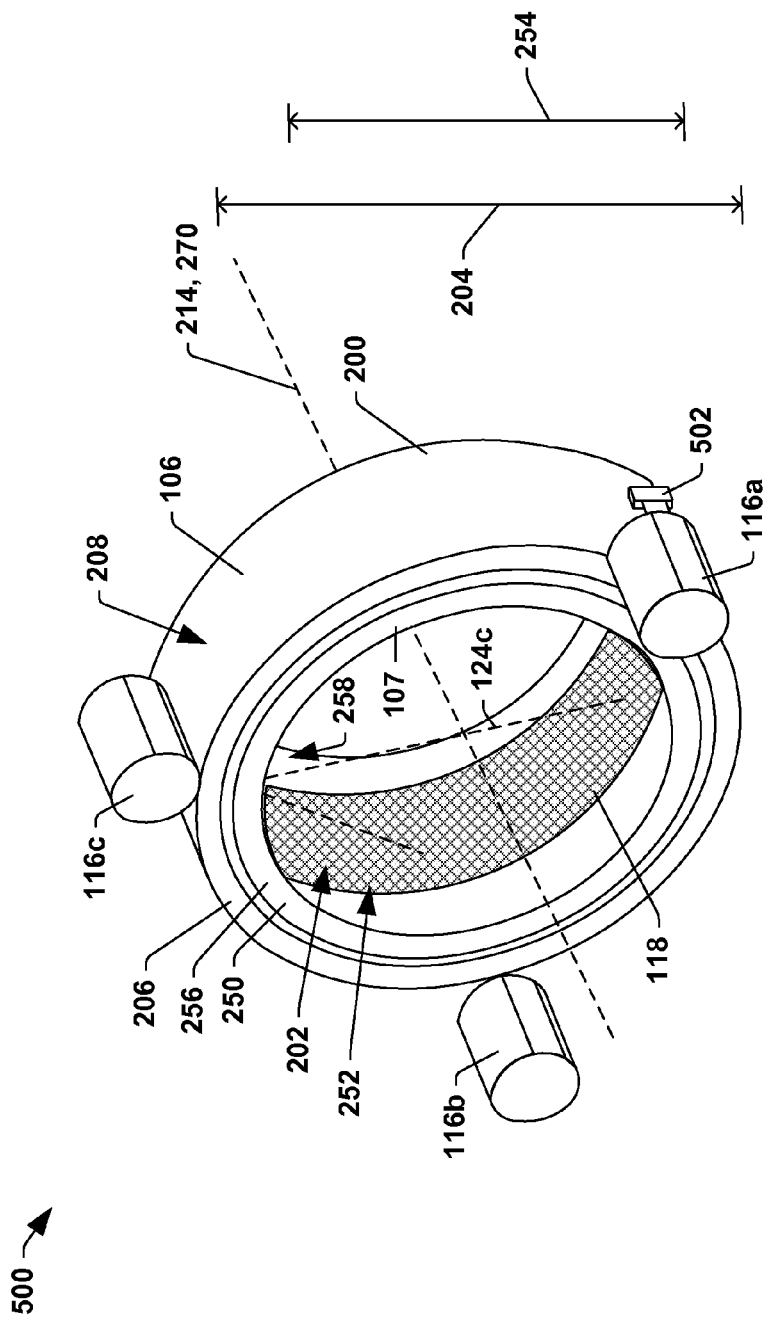
FIG. 5b illustrates a perspective view of an example examination unit.
Figure 5C:
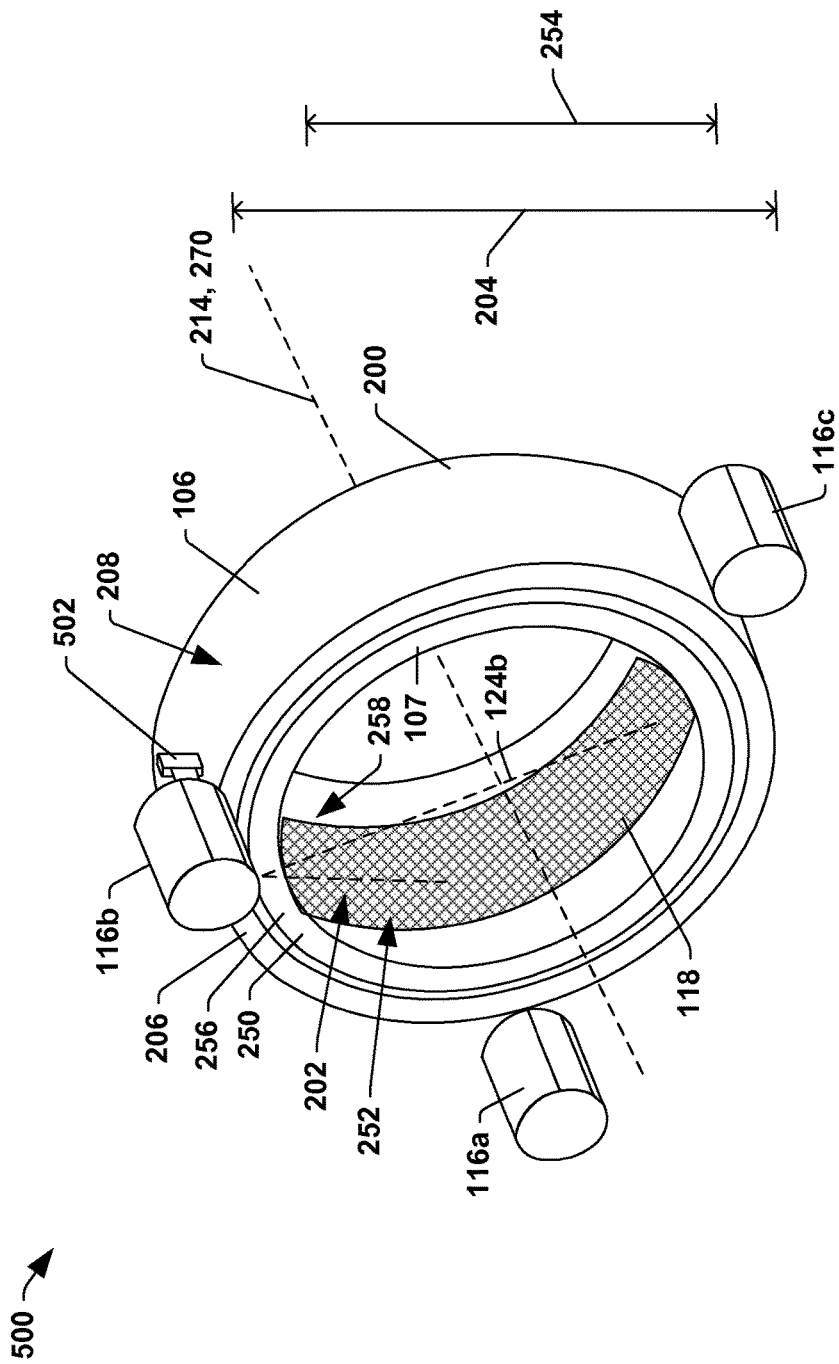
FIG. 5c illustrates a perspective view of an example examination unit.

Turning to FIGS. 5a to 5c, an example of a third examination unit 500 is illustrated. The third examination unit 500 may include some features of the examination unit 102 described with respect to FIGS. 1 to 3. For example, the third examination unit 500 may include the first rotating unit 106, the second rotating unit 107, the first drum 200, the second drum 250, etc.

In the illustrated example, the first rotating unit 106 may include the first radiation source 116a, the second radiation source 116b, and the third radiation source 116c, although any number of radiation sources are contemplated. In this example, the radiation sources 116a to 116c may be attached to/supported by the first drum 200. For example, one or more of the radiation sources 116a to 116c may be supported in a cantilever fashion. In this example, the first radiation source 116a and the second radiation source 116b project laterally outwardly from the outer surface 208 of the first drum 200 (e.g., or first disk). In an example, an attachment structure 502 is provided to attach the first and second radiation sources 116a and 116b to the first drum 200. The attachment structures 502 (e.g., two total in this example) may be attached/fixed to the outer surface 208 of the first drum 200, with the first and second radiation sources 116a and 116b attached to and extending from the attachment structures 502.

In the illustrated example, the third radiation source 116c may be attached directly to the first drum 200 in a similar manner as described with respect to FIGS. 2a and 2b. Radiation from the third radiation source 116c may pass through the third opening 210c of the first rotating unit 106. While the third radiation source 116c is not supported in the cantilevered fashion in this example, the third examination unit 500 is not so limited. Rather, in other examples, the first radiation source 116a may be attached directly to the first drum 200 (e.g., as described with respect to FIGS. 2a and 2b) while the second radiation source 116b and the third radiation source 116c are supported in the cantilevered fashion. In another example, the second radiation source 116b may be attached directly to the first drum 200 (e.g., as described with respect to FIGS. 2a and 2b) while the first radiation source 116a and the third radiation source 116c are supported in the cantilevered fashion. In further examples, two of the radiation sources 116a to 116c may be attached directly to the first drum 200 while one of the radiation sources 116a to 116c may be supported in the cantilevered fashion. Any number of sources attached in any such fashion(s) is contemplated.

It will be appreciated that the third examination unit 500 is not limited to including the illustrated attachment structures 502 for attaching/fixing the first and second radiation sources 116a and 116b to the first drum 200. Rather, any number of example structures may be provided, including fasteners, adhesives, or the like, such that the first radiation source 116a and the second radiation source 116b are supported in a cantilever fashion with respect to the first drum 200. Indeed, in some possible examples, the radiation sources 116a to 116c are not limited to being attached to the outer surface 208, and, instead, may be attached to/project from a side surface, an inner surface, etc. of the first drum 200.

In operation, the first radiation source 116a, the second radiation source 116b, and the third radiation source 116c can be oriented/directed inwardly toward the inner surface 258 of the second sidewall 256. In the illustrated example of FIG. 5a, the first radiation source 116a is substantially diametrically opposed from the detector array 118. By being oriented/directed toward the inner surface 258, the first radiation source 116a can generate the first radiation 124a within the first radiation spectrum, with the first radiation 124a directed toward the detector array 118.

Turning to FIG. 5b, another position of the first rotating unit 106 with respect to the second rotating unit 107 is illustrated. In this example, the third radiation source 116c is substantially diametrically opposed from the detector array 118. By being oriented/directed toward the inner surface 258, the third radiation source 116c can generate the third radiation 124c within the third radiation spectrum, with the third radiation 124c directed toward the detector array 118.

Turning to FIG. 5c, another position of the first rotating unit 106 with respect to the second rotating unit 107 is illustrated. In this example, the second radiation source 116b is substantially diametrically opposed from the detector array 118. By being oriented/directed toward the inner surface 258, the second radiation source 116b can generate the second radiation 124b within the second radiation spectrum, with the second radiation 124b directed toward the detector array 118.

It is to be appreciated that while FIGS. 5a to 5c illustrated three positions of the first rotating unit 106 with respect to the second rotating unit 107, in other examples, any number of relative positions between the first rotating unit 106 with respect to the second rotating unit 107 are envisioned. For example, the first rotating unit 106 and the second rotating unit 107 of the third examination unit 500 can rotate in a similar or identical manner as described and illustrated with respect to FIGS. 3a to 3e. Similarly, in some examples, the first rotating unit 106 is not limited to including the three radiation sources 116a to 116c, and, in other examples, may include two radiation sources 116a and 116b. In such an example, the first rotating unit 106 and the second rotating unit 107 can rotate with respect to one another in a similar or identical manner as described and illustrated with respect to FIG. 4. Moreover, the detector array may be cantilevered from the second rotating unit 107 (e.g., or a second disk) in a manner similar to the way in which the radiation sources are cantilevered from the first rotating unit 106, for example. In such an embodiment where the detector array is cantilevered, one or more of the radiation sources may or may not be cantilevered as well.

By providing the examination units 102, 400, 500 with a plurality of rotating units (e.g., the first rotating unit 106 and the second rotating unit 107), the radiation sources 116 and the detector array 118 can be rotated asynchronously relative to one another. That is, the first rotating unit 106 may be rotated asynchronously relative to the second rotating unit 107 such that a relative position between the radiation sources 116 and the detector array 118 is varied during an examination. By providing separate rotating units 106, 107, the radiation sources 116 and the detector array 118 can be rotated at different speeds. For example, the first rotating unit 106, which supports the radiation sources 116, can be rotated at the first rotational speed 300. The second rotating unit 107, which supports the detector array 118, can be rotated at the second rotational speed 302, with the second rotational speed 302 being greater than or less than the first rotational speed 300.

By having two separate rotating units 106, 107, the radiation sources 116 may no longer act as a constraint on the maximum rotational speed of the detector array 118. Furthermore, since a plurality of radiation sources 116 (e.g., the first radiation source 116a, the second radiation source 116b, and the third radiation source 116c) are provided within the first rotating unit 106, the detector array 118 can be exposed to the plurality of radiation sources 116, thus increasing the speed of examination.

In some examples, a method of operation may be provided. Such an example method may be used in association with some or all of the features illustrated in FIGS. 1 to 5. In this example, the method may include rotating the first rotating unit 106 comprising one or more radiation sources (e.g., the first radiation source 116a, the second radiation source 116b, the third radiation source 116c, etc.) at the first rotational speed 300. The method may include rotating the second rotating unit 107 comprising the detector array 118 at the second rotational speed 302 that is different than the first rotational speed 300. The method may include illuminating the detector array 118 via the first radiation source 116a of the one or more radiation sources during the first portion of the examination while the detector array 118 is at a first position relative to the first radiation source 116a. The method may include illuminating the detector array 118 via the second radiation source 116b of the one or more radiation sources during the second portion of the examination while detector array 118 is at a second position relative to the first radiation source 116*a*.

As used in this application, the terms "component", "module," "system", "interface", and the like are generally intended to refer to a computer-related entity, either hardware, a combination of hardware and software, software, or software in execution. For example, a component includes a process running on a processor, a processor, an object, an executable, a thread of execution, a program, or a computer. By way of illustration, both an application running on a controller and the controller can be a component. One or more components residing within a process or thread of execution and a component may be localized on one computer or distributed between two or more computers.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B and/or both A and B. Furthermore, to the extent that "includes", "having", "has", "with", or variants thereof are used, such terms are intended to be inclusive in a manner similar to the term "comprising".

Many modifications may be made to the instant disclosure without departing from the scope or spirit of the claimed subject matter. Unless specified otherwise, "first," "second," or the like are not intended to imply a temporal aspect, a spatial aspect, an ordering, etc. Rather, such terms are merely used as identifiers, names, etc. for features, elements, items, etc. For example, a first set of information and a second set of information generally correspond to set of information A and set of information B or two different or two identical sets of information or the same set of information.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above-described components (e.g., elements, resources, etc.), the terms used to describe such components are intended to correspond, unless otherwise indicated, to any component that performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A radiation system, comprising:
   a first rotating unit defining a first bore and configured to rotate about a first axis of rotation and comprising a first radiation source configured to generate radiation, wherein the radiation is at least one of x-ray radiation or gamma radiation; and
   a second rotating unit defining a second bore and configured to rotate about a second axis of rotation, wherein:
   the second rotating unit comprises a detector array configured to detect at least a portion of the radiation, and
   the first rotating unit is configured to rotate about the first axis of rotation at a first rotational speed and the second rotating unit is configured to concurrently rotate about the second axis of rotation at a second rotational speed different than the first rotational speed such that a relative position between the first radiation source and the detector array is varied while the first rotating unit is rotating at the first rotational speed and the second rotating unit is rotating at the second rotational speed.

2. The radiation system of claim 1, wherein:
   the first rotating unit comprises a second radiation source, and
   the second rotating unit comprises an aperture selected in size to expose the first radiation source to the detector array while the second radiation source is concealed from the detector array by the second rotating unit.

3. The radiation system of claim 2, wherein the first radiation source is configured to generate radiation within a first radiation spectrum and the second radiation source is configured to generate radiation within a second radiation spectrum different than the first radiation spectrum.

4. The radiation system of claim 1, wherein the first axis of rotation and the second axis of rotation are the same.

5. The radiation system of claim 1, wherein the first rotating unit comprises a second radiation source and a third radiation source.

6. The radiation system of claim 5, wherein:
   the second rotating unit comprises an aperture, and
   the aperture is selected in size to expose the first radiation source and the second radiation source.

7. The radiation system of claim 1, wherein the first bore has a first diameter and the second bore has a second diameter different than the first diameter.

8. The radiation system of claim 7, wherein the first diameter is greater than the second diameter.

9. The radiation system of claim 1, wherein a data acquisition component is configured to generate volumetric data based upon the at least a portion of the radiation detected by the detector array.

10. A radiation system, comprising:
    a first rotating unit defining a first bore and configured to rotate about a first axis of rotation and comprising a first radiation source configured to generate radiation, wherein the radiation is at least one of x-ray radiation or gamma radiation; and
    a second rotating unit defining a second bore and configured to rotate about a second axis of rotation, wherein:
    the second rotating unit comprises a detector array configured to detect at least a portion of the radiation, the first rotating unit is configured to rotate about the first axis of rotation in a first direction and the second rotating unit is configured to concurrently rotate about the second axis of rotation in a second direction opposite to the first direction such that a relative position between the first radiation source and the detector array is varied while the first rotating unit is rotating in the first direction and the second rotating unit is rotating in the second direction.

11. The radiation system of claim 10, wherein the first radiation source is configured to generate radiation within a first radiation spectrum and the first rotating unit comprises a second radiation source configured to generate radiation within a second radiation spectrum.

12. The radiation system of claim 11, wherein the first radiation source illuminates the detector array during a first portion of an examination and the second radiation source illuminates the detector array during a second portion of the examination, the first radiation spectrum substantially equal to the second radiation spectrum.

13. The radiation system of claim 11, wherein at least a portion of the second rotating unit comprises a radiation transparent material such that radiation emitted by the first radiation source traverses the second rotating unit.

14. The radiation system of claim 10, wherein:
the second rotating unit comprises an aperture through which the first radiation source emits the radiation toward the detector array.

15. A radiation system, comprising:
a first rotating unit defining a first bore and configured to rotate about a first axis of rotation and comprising a first radiation source configured to generate radiation, wherein the radiation is at least one of x-ray radiation or gamma radiation; and
a second rotating unit configured to be positioned within the first bore, wherein:
the second rotating unit defines a second bore into which an object is positioned during an examination,
the second rotating unit is configured to rotate about a second axis of rotation, and
the second rotating unit comprises a detector array configured to detect at least a portion of the radiation generated by the first radiation source, and
the first rotating unit is configured to rotate about the first axis of rotation at a first rotational speed and the second rotating unit is configured to concurrently rotate about the second axis of rotation at a second rotational speed different than the first rotational speed such that a relative position between the first radiation source and the detector array is varied while the first rotating unit is rotating at the first rotational speed and the second rotating unit is rotating at the second rotational speed.

16. The radiation system of claim 15, wherein the second rotating unit comprises an aperture through which the at least a portion of the radiation detected by the detector array passes.

17. The radiation system of claim 16, wherein the detector array is substantially diametrically opposed from the aperture.

18. The radiation system of claim 15, wherein the first radiation source is configured to generate radiation within a first radiation spectrum and the first rotating unit comprises a second radiation source configured to generate radiation within a second radiation spectrum, and wherein the first radiation source illuminates the detector array during a first portion of an examination and the second radiation source illuminates the detector array during a second portion of the examination, the first radiation spectrum substantially equal to the second radiation spectrum.

19. The radiation system of claim 15, wherein the first rotational speed is less than the second rotational speed.

20. The radiation system of claim 15, wherein:
the first rotating unit comprises a second radiation source, and
the second rotating unit comprises an aperture selected in size to expose the first radiation source to the detector array while the second radiation source is concealed from the detector array by the second rotating unit.

* * * * *